United States Patent
Ryan (10) Patent No.: US 12,064,288 B2
(45) Date of Patent: Aug. 20, 2024

(54) DISTANCE, DIAMETER AND AREA DETERMINING DEVICE

(71) Applicant: Provisio Medical, Inc., San Diego, CA (US)

(72) Inventor: Stephen Eric Ryan, San Diego, CA (US)

(73) Assignee: Provisio Medical, Inc., San Diego, CA (US)

( * ) Notice: Subject to any disclaimer, the term of this patent is extended or adjusted under 35 U.S.C. 154(b) by 0 days.

(21) Appl. No.: 16/264,449

(22) Filed: Jan. 31, 2019

(65) Prior Publication Data

US 2019/0175148 A1 Jun. 13, 2019

Related U.S. Application Data

(63) Continuation of application No. 14/214,297, filed on Mar. 14, 2014, now Pat. No. 10,231,701.

(Continued)

(51) Int. Cl.
*A61B 8/08* (2006.01)
*A61B 5/00* (2006.01)
(Continued)

(52) U.S. Cl.
CPC .......... *A61B 8/5261* (2013.01); *A61B 5/0066* (2013.01); *A61B 5/0084* (2013.01);
(Continued)

(58) Field of Classification Search
CPC ..... A61B 8/5261; A61B 8/4488; A61B 8/463; A61B 8/0891; A61B 5/6852;
(Continued)

(56) References Cited

U.S. PATENT DOCUMENTS 3,542,014 A 11/1970 Peronneau
4,841,977 A 6/1989 Griffith et al.
(Continued)

FOREIGN PATENT DOCUMENTS

WO WO-2016039761 A1 3/2016

OTHER PUBLICATIONS

EP14901802.0 Extended European Search Report dated Sep. 18, 2018.
(Continued)

*Primary Examiner* — Baisakhi Roy
*Assistant Examiner* — Kaitlyn E Sebastian
(74) *Attorney, Agent, or Firm* — KNOBBE MARTENS OLSON & BEAR LLP (57) ABSTRACT

The invention describes a novel implementation of ultrasound or OCT technology to approximate the dimensions of fluid-filled structures (when using ultrasound technology) or other structures (when using OCT technology). The invention in a preferred embodiment is an elongated member such as a catheter that uses ultrasound or OCT technology to approximate the dimensions of a structure into which the catheter has been placed. In a preferred embodiment, the catheter includes multiple ultrasound transducers arranged in an annular or circumferential configuration on, embedded into or within the body of the elongated member so that distance measurements can be obtained between the elongated member and the wall of the immediately facing structure (e.g., a fluid-filled lumen). Utilizing these measurements, the present invention approximates for the physician the shape and size of the structure into which the elongated member is placed. The invention also includes a method for producing three-dimensional images from two-dimensional images.

20 Claims, 5 Drawing Sheets

Related U.S. Application Data (60) Provisional application No. 61/801,438, filed on Mar. 15, 2013.

(51) Int. Cl.
| | | |
|---|---|---|
| *A61B 5/107* | (2006.01) | |
| *A61B 8/00* | (2006.01) | |
| *A61B 8/12* | (2006.01) | |
| *A61F 2/958* | (2013.01) | |
| *A61B 5/055* | (2006.01) | |
| *A61B 6/00* | (2006.01) | |
| *A61B 6/03* | (2006.01) | |

(52) U.S. Cl.
CPC .......... *A61B 5/1076* (2013.01); *A61B 5/6852* (2013.01); *A61B 8/0891* (2013.01); *A61B 8/12* (2013.01); *A61B 8/445* (2013.01); *A61B 8/4488* (2013.01); *A61B 8/4494* (2013.01); *A61B 8/463* (2013.01); *A61B 8/5223* (2013.01); *A61F 2/958* (2013.01); *A61B 5/0035* (2013.01); *A61B 5/0095* (2013.01); *A61B 5/055* (2013.01); *A61B 5/1079* (2013.01); *A61B 6/032* (2013.01); *A61B 6/487* (2013.01); *A61B 8/483* (2013.01); *A61B 8/54* (2013.01)

(58) Field of Classification Search
CPC ..... A61B 5/0066; A61B 5/0084; A61B 8/445; A61B 8/12; A61B 8/4494; A61B 8/5223; A61B 5/1076; A61B 5/0035; A61B 5/055; A61B 6/032; A61B 6/487; A61B 8/483; A61B 5/0095; A61B 8/54; A61B 5/1079; A61F 2/958; G16H 50/30

See application file for complete search history.

(56) References Cited

U.S. PATENT DOCUMENTS

| | | | |
|---|---|---|---|
| 4,927,418 | A | 5/1990 | Dake et al. |
| 5,876,345 | A | 3/1999 | Eaton et al. |
| 6,059,731 | A | 5/2000 | Seward et al. |
| 6,175,757 | B1* | 1/2001 | Watkins .................. A61B 5/055 |
| | | | 128/916 |
| 6,375,615 | B1* | 4/2002 | Flaherty .................... A61F 2/95 |
| | | | 600/463 |
| 6,592,526 | B1* | 7/2003 | Lenker .................... A61B 8/12 |
| | | | 600/463 |
| 7,940,974 | B2* | 5/2011 | Skinner .................... G06T 7/12 |
| | | | 382/131 |
| 10,231,701 | B2 | 3/2019 | Ryan |
| 2005/0033182 | A1 | 2/2005 | Cerofolini |
| 2007/0038112 | A1* | 2/2007 | Taylor ...................... A61B 8/13 |
| | | | 600/459 |
| 2007/0088214 | A1 | 4/2007 | Shuros |
| 2007/0123776 | A1 | 5/2007 | Aharoni |
| 2007/0167823 | A1* | 7/2007 | Lee .......................... A61B 8/12 |
| | | | 600/463 |
| 2008/0091171 | A1* | 4/2008 | Strommer ................ A61B 6/12 |
| | | | 604/528 |
| 2009/0259174 | A1* | 10/2009 | Silver ...................... A61B 8/12 |
| | | | 604/35 |
| 2009/0299360 | A1 | 12/2009 | Ormsby |
| 2009/0318003 | A1* | 12/2009 | Hossack .................. A61B 8/12 |
| | | | 439/299 |
| 2010/0152590 | A1* | 6/2010 | Moore .................. A61B 8/4461 |
| | | | 600/466 |
| 2010/0168572 | A1* | 7/2010 | Sliwa .................. A61B 18/1492 |
| | | | 600/439 |
| 2010/0274136 | A1 | 10/2010 | Cerofolini |
| 2010/0305451 | A1 | 12/2010 | Kim et al. |
| 2011/0144491 | A1 | 6/2011 | Sliwa et al. |
| 2011/0203375 | A1 | 8/2011 | Farthing et al. |
| 2012/0004556 | A1* | 1/2012 | Rold ...................... A61B 8/463 |
| | | | 600/463 |
| 2012/0157841 | A1* | 6/2012 | Glaenzer ............ A61B 10/0241 |
| | | | 600/439 |
| 2013/0096409 | A1* | 4/2013 | Hiltner ...................... A61B 5/01 |
| | | | 600/381 |
| 2013/0231564 | A1* | 9/2013 | Zagorchev ........... A61B 8/5207 |
| | | | 600/447 |
| 2013/0289369 | A1* | 10/2013 | Margolis .................. A61B 5/01 |
| | | | 606/41 |
| 2014/0005521 | A1 | 1/2014 | Koehler et al. |
| 2014/0005553 | A1* | 1/2014 | Ryan .................... A61B 5/6853 |
| | | | 600/473 |
| 2014/0058294 | A1 | 2/2014 | Gross et al. |
| 2014/0163361 | A1 | 6/2014 | Stigall et al. |
| 2014/0180032 | A1 | 6/2014 | Millett et al. |
| 2014/0187925 | A1 | 7/2014 | Corl |
| 2014/0187960 | A1 | 7/2014 | Corl |
| 2015/0257732 | A1 | 9/2015 | Ryan |

OTHER PUBLICATIONS

U.S. Appl. No. 14/214,297 Notice of Allowance dated Oct. 30, 2018.
Office action dated Apr. 20, 2016 for U.S. Appl. No. 14/214,297.
Office action dated Nov. 17, 2017 for U.S. Appl. No. 14/214,297.
PCT/US2014/055274 International Search Report and Written Opinion dated Jan. 2, 2015.
Extended European Search Report issued on Jun. 29, 2023 in corresponding European Patent Application No. 22214475.0.

* cited by examiner

DISTANCE, DIAMETER AND AREA DETERMINING DEVICE

CROSS-REFERENCE TO RELATED APPLICATIONS

This application is a continuation of U.S. patent application Ser. No. 14/214,297, filed Mar. 14, 2014, which claims the benefit of U.S. Provisional No. 61/801,438, filed Mar. 15, 2013, the entire content of which are incorporated herein by reference

BACKGROUND OF THE INVENTION

1. Field of the Invention

The present invention relates generally to methods and medical devices that gather information about vessels, structures or devices in a body and more particularly to methods and medical devices for measuring dimensions of such vessels, structures or devices and calculate cross-sectional areas of such vessels, structures or devices.

2. Description of Related Art

Within the field of interventional cardiology, the utilization of coronary drug-eluting stents has significantly reduced stent failure and the need for revascularization. Recent imaging studies have illustrated that the predominate cause of residual stent failure is stent underexpansion and lesion edge problems such as undersizing the length of the stent needed to appropriately cover the lesion. The limitations of today's angiogram often do not allow the physician to adequately assess the lesion prior to stent placement or determine the degree of expansion of the deployed stent. This is a problem in need of a solution.

Current imaging catheters utilize ultrasound or optical technologies to provide a cross-section image that is then interpreted by the physician to determine, among other characteristics, the dimensions of the lumen surrounding the catheter. For example, Intravascular Ultrasound (IVUS) is commonly used in interventional diagnostic procedures to image blood vessels to locate and characterize atherosclerosis and other vessel diseases and defects. In use, a guidewire is placed in a vessel of interest. Then, an IVUS catheter is threaded over the guidewire and ultrasonic signals are sent from the catheter, bounced off the tissue, received by the catheter and passed from the catheter to a system. These ultrasound echoes are processed by the system to produce images of the vessel and its physiology.

Optical Coherence Tomography (OCT) systems are also used in interventional diagnostic procedures to image blood vessels to locate and characterize atherosclerosis and other vessel diseases and defects. In use, again a guidewire is placed in a vessel of interest. Then, an OCT catheter is threaded over the guidewire and light signals are sent from the catheter, bounced off the tissue, received by the catheter and passed from the catheter to a system. These light echoes are processed by the system to produce images of the vessel and its physiology.

These IVUS and OCT images and the information about the vessel, including vessel dimensions, is considerably more detailed than the information that is obtainable from traditional angiography images that which shows only a two-dimensional shadow of the vessel lumen. Examples of some of the information provided by IVUS or OCT systems include: determining a diameter of a vessel to be used in determining the correct diameter or a stent to be placed; determining the length of a physiological problem such as the presence of atherosclerotic material so that the correct length of a stent to be placed can be determined to dilate the stenosis; verifying that a stent, once placed, is well apposed against a vessel wall to minimize thrombosis and optimize drug delivery (in the case of a drug eluting stent); verifying that after a stent has been place, the diameter and luminal cross-section area of the stented vessel are adequate; and identifying an exact location of side-branch vessels to aid in stent placement or therapy delivery.

Although current IVUS and OCT systems provide additional and more detailed information compared to angiograms, these IVUS and OCT systems introduce significant additional time, cost and complexity into minimally invasive procedures. Further, the images produced by IVUS and OCT systems often are subject to interpretation of the physician. Thus, there is a need for an improved way to get information about a vessel or structure, particularly information about the diameter of a vessel or structure.

SUMMARY OF THE INVENTION

The invention describes a novel implementation of ultrasound or OCT technology to approximate the dimensions of fluid-filled structures (when using ultrasound technology) or other structures (when using OCT technology). The invention in a preferred embodiment is an elongated member such as a catheter that uses ultrasound or OCT technology to approximate the dimensions of a structure into which the catheter has been placed. In a preferred embodiment, the catheter includes multiple ultrasound transducers arranged in an annular or circumferential configuration on, embedded into or within the body of the elongated member so that distance measurements can be obtained between the elongated member and the wall of the immediately facing structure (e.g., a fluid-filled lumen). Utilizing these measurements, the present invention approximates for the physician the shape and size of the structure into which the elongated member is placed. The invention also includes a method for producing three-dimensional images from two-dimensional images.

The disclosed device, as used in accordance with the methods of the invention, ensures a simpler way of calculating cross-sectional dimensions and creating three-dimensional maps than prior art devices and techniques.

BRIEF DESCRIPTION OF THE DRAWINGS

The invention will be described hereafter in detail with particular reference to the drawings. Throughout this description, like elements, in whatever embodiment described, refer to common elements wherever referred to and reference by the same reference number. The characteristics, attributes, functions, interrelations ascribed to a particular element in one location apply to that element when referred to by the same reference number in another location unless specifically stated otherwise. In addition, the exact dimensions and dimensional proportions to conform to specific force, weight, strength and similar requirements will be within the skill of the art after the following description has been read and understood.

All figures and drawn for ease of explanation of the basic teachings of the present invention only; the extensions of the figures with respect to number, position, relationship and dimensions of the parts to form examples of the various

DETAILED DESCRIPTION OF THE INVENTION

In order that the invention may be clearly understood and readily carried into effect, preferred embodiments of the invention will now be described with reference to the accompanying drawings. The description of these embodiments is given by way of example only and not to limit the invention. The medical device of the present invention, in all of its embodiments, is shown in the drawings generally labeled 10. A preferred embodiment of the present invention being described herein is a catheter. But, the invention applies to many other devices where knowing the dimensions around the medical device 10 is desirable.

As mentioned above, although a preferred embodiment of the present invention is a catheter, the invention applies to many other devices where it is desirable to know the cross-sectional dimensions the space surrounding the medical device 10. Examples of such medical devices 10 include, but are not limited to, conventional intravascular ultrasound (IVUS), optical coherence tomography (OCT) and photoacoustic imaging systems, image guided therapeutic devices or therapeutic delivery devices, diagnostic delivery devices, Forward-Looking IVUS (FLIVUS), intracardiac echocardiography (ICE), forward looking ICE, optical light-based imaging (e.g., endoscopes), pressure sensing wires, high intensity focused ultrasound (HIFU), radiofrequency, thermal imaging or thermography, electrical impedance tomography, elastography, orthopedic and spinal imaging and neurological imaging.

Figure 1:
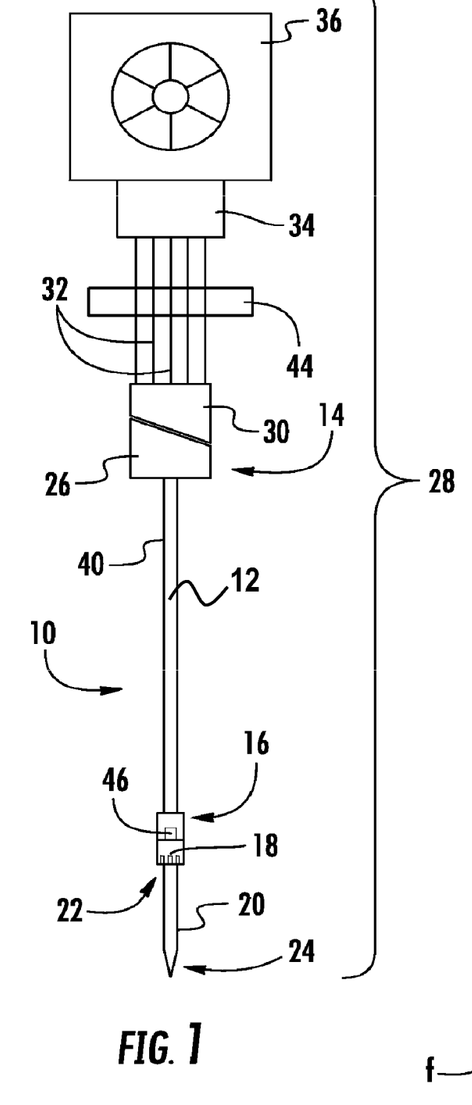
FIG. 1 is a side schematic view of a preferred embodiment of the catheter of the present invention.

As shown in FIG. 1, the medical device 10 of the present invention includes a body member 12 having a proximal end 14 and a distal end 16. The medical device 10 includes a plurality of transducers 18. In a preferred embodiment, the medical device 10 also includes an elongated tip 20 having a proximal end 22 and a distal end 24. The medical device 10 includes a proximal connector 26. In an embodiment of the invention, the medical device 10 is part of a system 28 that includes a distal connector 30, electrical conductors 32, a data acquisition unit 34 and a computer 36.

In a preferred embodiment of the medical device 10 shown in FIGS. 1-5, the body member 12 is tubular and has a central lumen 38. In a preferred embodiment of the medical device 10, the body member 12 has a diameter of about 650 .mu.m. This dimension is illustrative and not intended to be limiting. In embodiments of the medical device 10, the diameter of the medical device 10 will depend on the type of device that medical device 10 is and where the medical device 10 will be used, as is well understood in the art.

The proximal end 14 of the body member 12 is attached to the proximal connector 26. In the embodiment of medical device 10 that includes an elongated tip 20, proximal end 22 of the elongated tip 20 is attached to the distal end 16 of the body member 12. The elongated tip 20, where employed, allows the catheter 20 to be moved along a rapid exchange device, were employed as described below, adds flexibility to the distal end of the medical device 10 to allow easier maneuvering of the medical device 10, particularly in vessels, and allows the transducers 18, in certain embodiments, to be more precisely located in the vessel or other structure where the medical device 10 is placed.

The body member 12 and elongated tip 20 are made of resilient flexible biocompatible material such as is common for IVUS catheters as is well understood by those skilled in the art. Medical device 10 is preferably tubular with a central lumen 38 but may also not have a central lumen 38. Further, medical device 10 may have one or more lumens in addition to central lumen 38. Preferably, the outer diameter of the body member 12 and elongated tip 20, if present, is substantially constant along its length. But, neither the body member 12 nor elongated tip 20 is required to have a substantially constant diameter.

The transducers 18 in embodiments of the medical device 10 using ultrasound are preferably conventional piezoelectric transducers such as are typically used on IVUS catheters. These piezoelectric transducers are built from piezoelectric ceramic material and covered by one or more matching layers that are typically thin layers of epoxy composites or polymers. In addition, other transducer technologies may be used to create transducers 18 including, but not limited to, PMUT (Piezoelectric Micromachined Ultrasonic Transducer), CMUT (Capacitive Micromachined Ultrasonic Transducer) and photoacoustic technologies. The medical device 10 of the present invention may be of the rotational type or solid state (non-rotational type) such as are commonly in use in connection with IVUS imaging systems.

Further, the operating frequency for the ultrasound transducers 18 is typically in the range of from about 8 to about 50 MHz, depending on the dimensions and characteristics of the transducer. Generally, higher frequency of operation provides better resolution and a smaller medical device 10. But, the price for this higher resolution and smaller catheter size is a reduced depth of penetration into the tissue of interest and increased echoes from the blood itself (making the image more difficult to interpret). Lower frequency of operation is more suitable for imaging in larger vessels or within structures such as the chambers of the heart. Although specific frequency ranges have been given, this range is illustrative and not limiting. The ultrasonic transducers 18 may produce and receive any frequency that leaves the transducer 18, impinges on some structure or material of interest and is reflected back to and picked up by the transducer 18.

The medical device 10 may, in some embodiments, use optical coherence tomography (OCT) transducers 18. These OCT transducers produce light in the near infrared range that leaves the transducer 18, impinges on some structure or material of interest and is reflected back to and picked up by the transducer 18. In some embodiments of these OCT transducers 18, the light is produced by a laser or other coherent light source outside of the medical device 10 and passed to the medical device 10 via fiber optic strands through the proximal connector 26 and ultimately to the location of the transducers 18 near the distal end 16 of the body member 12. In other embodiments of the medical device 10 that uses OCT transducers 18, the light needed for the transducers 18 is produced on the medical device 10 itself (e.g., at or near the proximal end 14 of the body member 12 by, for example, laser diodes) or at the site of the transducers 18 themselves as, for example, by laser diodes. Also, these transducers 18 have been described as having been of the OCT type. But, any transducers 18 that use coherent light or electromagnetic radiation may be used.

Regardless of whether the transducers are of the ultrasound or OCT type, the transducers 18 may be located on the outer surface 40 of the body member 12, within the material of the body member 12, on the surface of the central lumen 38 or within the central lumen 38. In those embodiments where the transducers 18 are not located on the outer surface 40 of the body member 12, the material of the body member 12 must be transparent to the ultrasonic waves or light emitted from or returning to the transducers 18 or the ultrasonic waves or light emitted from or returning to the transducers 18 may pass through windows in the material of the body member 12.

Figure 4A:
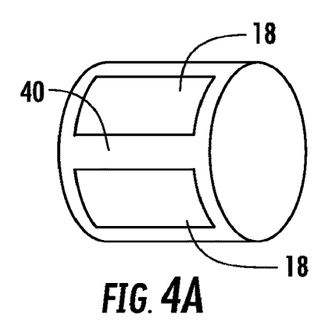
FIG. 4A and FIG. 4B are perspective views of a switch and a single array of transducers of an alternate embodiment of the catheter of the present invention.
Figure 4B:
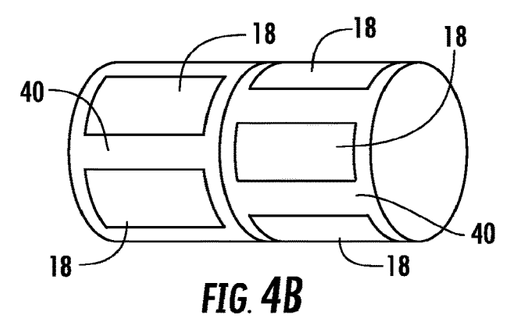

In the medical device 10 of the invention, two or more transducers 18 are arranged in a single annular or circumferential ring around or within the body member 12 (FIG. 4A) or can be an array of multiple annular or circumferential rings located one behind the other (FIG. 4B). Where the medical device 10 includes an array of transducers 18 such as is shown in FIG. 4B, the transducers 18 in one annular or circumferential group are preferably, although not required to be, staggered with respect to the transducers 18 in the annular or circumferential group located either more proximal or distal to it. Further, although arrays of two annular or circumferential groups of transducers 18 are shown, any number of annular or circumferential groups of transducers 18 may be used.

As stated, the circumferential arrays of transducers 18 are axially separated along the body member 12. In one configuration of the circumferential arrays of transducers 18, the transducers 18 in one array are aligned with the transducers 18 in the adjacent array along the elongated axis of the body member 12. In another, preferred embodiment of the medical device 10 shown in FIG. 4B, the transducers 18 in one array are staggered with respect to the transducers 18 in the adjacent array. "Staggered" means that the transducers 18 in one array are not aligned with the transducers 18 in the adjacent array along the axis of the body member 12.

In the preferred embodiment of the medical device 10 of FIG. 4B, the transducers 18 in one array overlap with the transducers 18 in the adjacent array so that a very compact configuration of transducers 18 is produced. For example, by way of illustration, the medical device 10 could have two arrays of transducers 18 where the transducers 18 are staggered with respect to the transducers 18 of the adjacent array (FIG. 4B) and the centers of the transducers 18 of one array are spaced from the centers of the transducers 18 of the other array by a distance, for example, of about 250 .mu.m. This dimension is illustrative and not intended to be limiting. Further, although the preferred embodiment of the medical device 10 has the transducers 18 of one array overlapping with the transducers 18 of the adjacent array, these transducers 18 are not required to be overlapping.

This embodiment of the medical device 10 where one circumferential array of transducers 18 is off-set from and overlapping or interlaced with the adjacent array of transducers 18 allows each transducer 18 to have sufficient surface area to be effective because the distance between the centers of each transducer 18 is minimized. As a result, the staggering and in some cases the interlacing of the transducers 18 allows all the transducers 18 to fit within a small circumference as required when the transducers 18 are utilized on small medical devices 10 such as a 0.035" or 0.018" wire or even a 0.014" wire such as would be used in coronary guidewire such as much pass through the lumen tube of an angioplasty catheter which is approximately 650 um in size.

The surface shape of the transducers 18 can be circles, ovals, squares, rectangles, triangles, wedges, or similar shapes. The distance between centers of each ultrasound transducer 18 can be as large as 1-2 mm without being significant to vascular measurements although distances less than 1 mm are preferable and even more preferable is less than 500 um. At center-spacing distances of 500 um or less, the distance measurements produced by the transducers 18 will not be meaningfully altered by the fact that the transducers 18 in adjacent arrays of transducers 18 are not circumferentially aligned.

Figure 2:
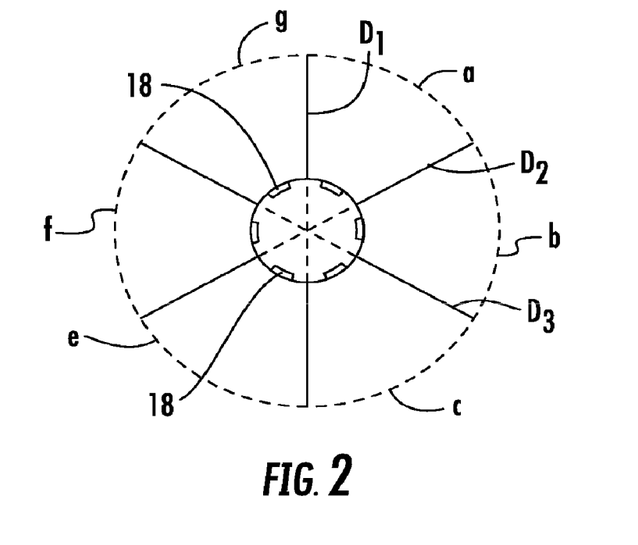
FIG. 2 is an end view of an alternate embodiment of the catheter of the present invention.
Figure 6:
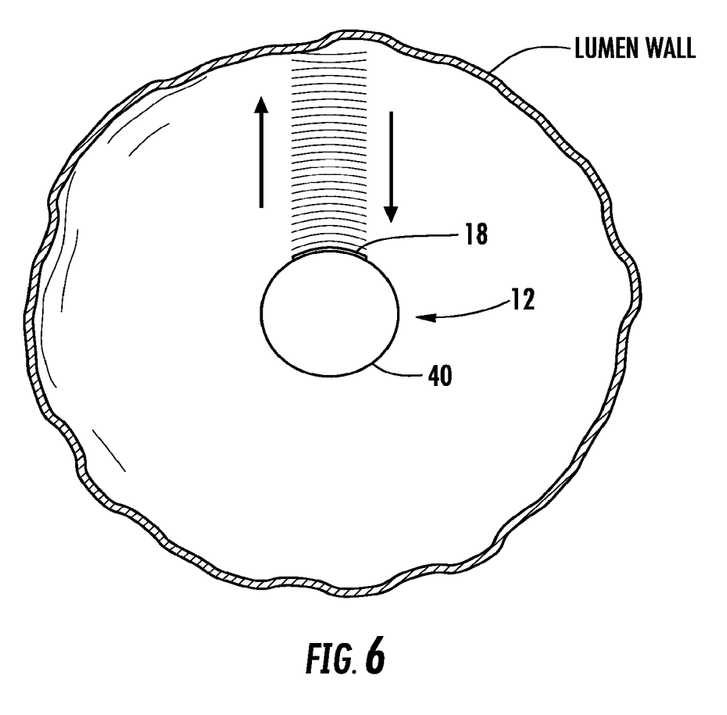
FIG. 6 is an end schematic view of the catheter of an embodiment of the present invention used to determine the cross-sectional area of a structure.

As shown in FIG. 6, each of the transducers 18, when energized, emits an ultrasonic wave or light that is directed away from the transducer 18 and thus from the body member 12. As shown in FIG. 2, because the transducers 18 are located in an annular or circumferential fashion around the body member 12, the ultrasonic waves or light they emit are directed away from the body member 12 in non-parallel paths. The transducers 18 may be energized to emit ultrasonic waves or light simultaneously or may be energized selectively (e.g., sequentially around the circumference of the body member 12 or in any other selective fashion).

The transducers 18 can be individually connected to electrical conductors 32 to connect the transducers 18 to the proximal connector 26. In certain embodiments, each transducer 18 needs an electrical pulses to energize the transducer 18 and the ability to deliver received echo signals from the transducer 18 electrically to a computer 36 or Patient Interface Module (PIM) 44 to be analyzed (during the intervals between transmit pulses). Where a PIM 44 is used, the PIM is located along the path between the medical device 10 and computer 36 and may include the distal connector 30. The computer 36 or PIM 44 controls the electrical or optical pulses sent to the transducer 18, processes, amplifies, filters or aggregates the data, interprets the signal coming back from the transducer 18 after the transducer 18 picks up the received echoes from the emitted pulses, produces images, makes calculations including calculations of dimensions and performs co-registration of images, data and calculations produced by the computer 36 with other images, data and calculations.

The electrical conductors 32 in certain embodiments run from the transducers 18 to the proximal connector 26 and may run within the material of the body member 12 or along its outer surface 40 or along or within the central lumen 38 to conduct the electrical excitation provided to the proximal connector 26 to the transducer 18 and return the signal from the transducer 18 thereafter to the proximal connector 26. Electrical conductors 32 also carry signals from the transducers 18 to the computer 36 or PIM 44. The electrical conductors 32 may be wires including twisted pair wire, coaxial cable, fiber optics, wave guides and other wire media as is well understood in the art.

In other embodiments of the medical device 10, particularly those embodiments using OCT technology, optical fibers carry energy to the transducers 18 and signals from the transducers 18 to the computer 36 or PIM 44 or both. In a variant embodiment applicable to both ultrasound and OCT systems, electrical energy may be carried to the transducers 18 via electrical conductors 32 and the signal of the received echoes sent back from the transducers 18 to the computer 36 or PIM 44 via optical fibers.

Further, although in some embodiments of the medical device 10, the transducers 18 send their signals to the computer 36 or PIM 44 through electrical conductors 32 or optical fibers, in other embodiments, the transducers 18 communicate their signals to the computer 36 or PIM 44 through wireless communication means well known to those skilled in the art including but not limited to acoustic, RF and infrared technology.

Figure 5:
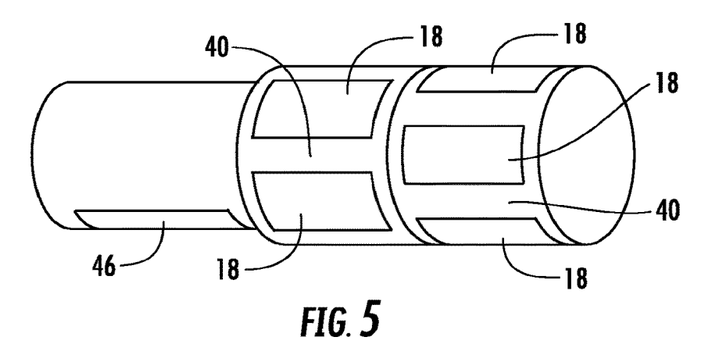
FIG. 5 is a perspective view of the catheter of the present invention in use in a vessel.

Alternately, as shown in FIG. 5, the transducers 18 can be connected to an electrical switch 46 located between the electrical conductors 32 and the transducers 18. The electrical switch 46 reduces the number of necessary electrical conductors 32 by having fewer lines travel from the proximal connector 26 to the switch 46 and then having the electrical energy carrying ability of the few line expanded through the switch to reach the multitude of transducers 18. Further, additional electrical conductors 32 or optical fibers can be added to control the electrical switch 46. In a preferred embodiment of switch 46, switch 46 is a multiplexer such as is well understood in the art. The use of a multiplexer reduces the number of electrical conductors 32 or optical fibers passing from the proximal connector 26 through the body member 12 to the transducers 18 and in some cases, provides additional control functions.

Figure 3A:
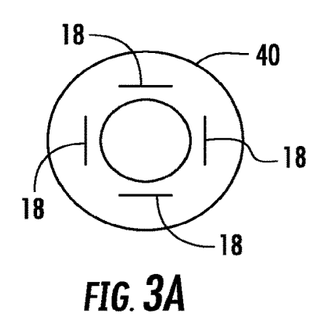
FIG. 3A, FIG. 3B and FIG. 3C are end views of the transducer arrays of alternate embodiments of the catheter of the present invention.
Figure 3B:
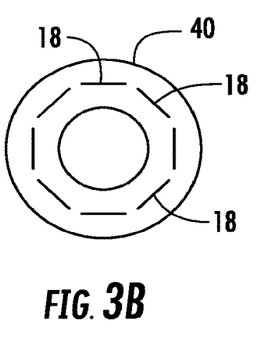
Figure 3C:
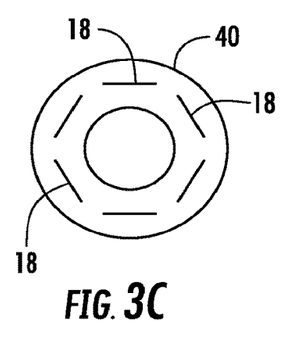

Preferably, four (FIG. 3A) to 12 transducers 18 are used for measurements in a medical device 10. More preferably, six (FIG. 3C) to ten transducers 18 will be utilized (FIG. 3B showing eight transducers 18). Where the medical device 10 is a coronary catheter, because of the need to keep the medical device 10 small in order to fit into the small coronary arteries, each transducer 18 will preferably have an area of less than about 1 mm$^2$. The number of transducers 18, as well as the dimensions given, are for illustration purposes only and not intended to be limiting. Any number of two or more transducers 18 as well as any practical dimensions for the transducers 18 may be used as technology allows and as desired by those skilled in the art.

Where the medical device 10 is part of a system 28, in addition to the medical device 10 described above, the system 28 will further include the computer 36 or PIM 44 or both (instead of just having the medical device 10 connected to the computer 36 or PIM 44). Where the medical device 10 is part of a system 28, a distal connector 30 mates with the proximal connector 26, as is well understood in the art, to connect the medical device 10 to the rest of the system 28. Electrical conductors 32 carry the control signals or energy or both to the distal connector 30 where the control signals, energy or both are passed to the proximal connector 26 to be used by the medical device 10.

The system 28 also preferably includes a data acquisition unit 34 that may be part of or separate from the computer 36 or PIM 44. The data acquisition unit 34 converts the analog data produced by the transducers 18 into digital data that can be processed by the computer 36 or PIM 44. As mentioned, the data acquisition unit 34 may be part of or separate from either the computer 36 of PIM 44. In addition, the data acquisition unit 34 may be part of the medical device 10 itself or may be located in the distal connector 30 or elsewhere along the path from the distal connector 30 to the computer 34 or PIM 44.

Figure 7:
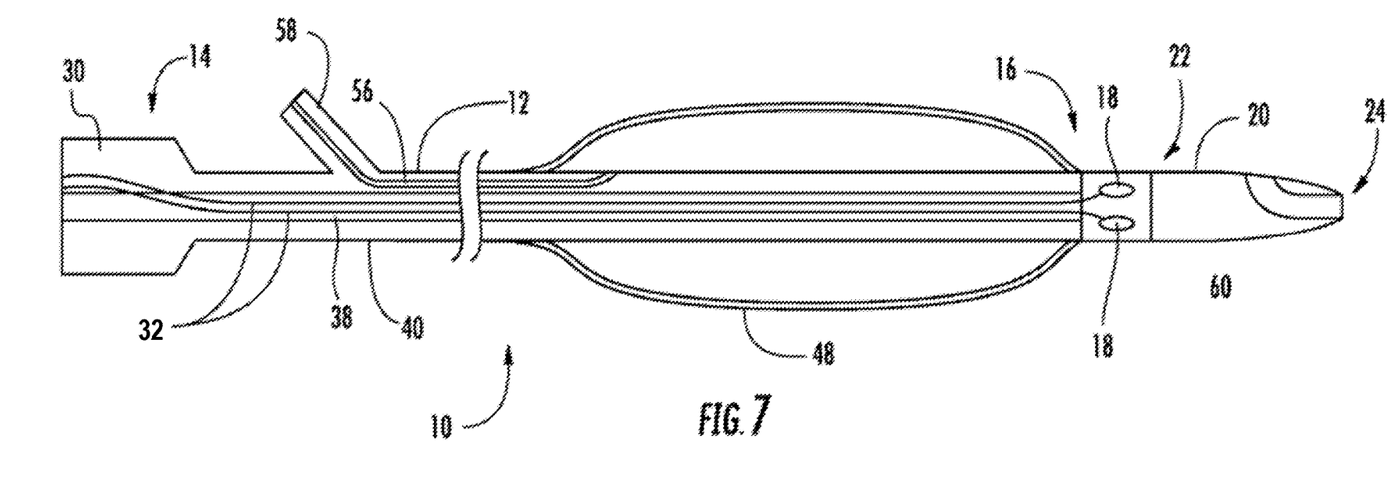
FIG. 7 is a side schematic view of an embodiment of the catheter of the present invention having an angioplasty balloon.

In an embodiment of the medical device 10 shown in FIG. 7, an angioplasty balloon 48 is placed on or around the body member 12 as is well understood in the art. In this embodiment, the transducers 18 are preferably placed distal to the angioplasty balloon 48. In another embodiment of the medical device 10 shown in FIG. 8, a stent delivery balloon and stent assembly 50 is placed on or around the body member 12 as is well understood in the art. In this embodiment, the stent delivery balloon and stent assembly 50 includes a stent delivery balloon 52 and a stent 54. The transducers 18 are also preferably placed distal to the stent delivery balloon and stent assembly 50. In either of these embodiments, the medical device 10 includes a duct 56 that travels along the length of the body member 12 from the respective balloons and ends in an inflation port 58. Balloon 48 or the balloon of the stent delivery balloon and stent assembly 50 may be selectively inflated and deflated via the inflation port 58.

Figure 9:
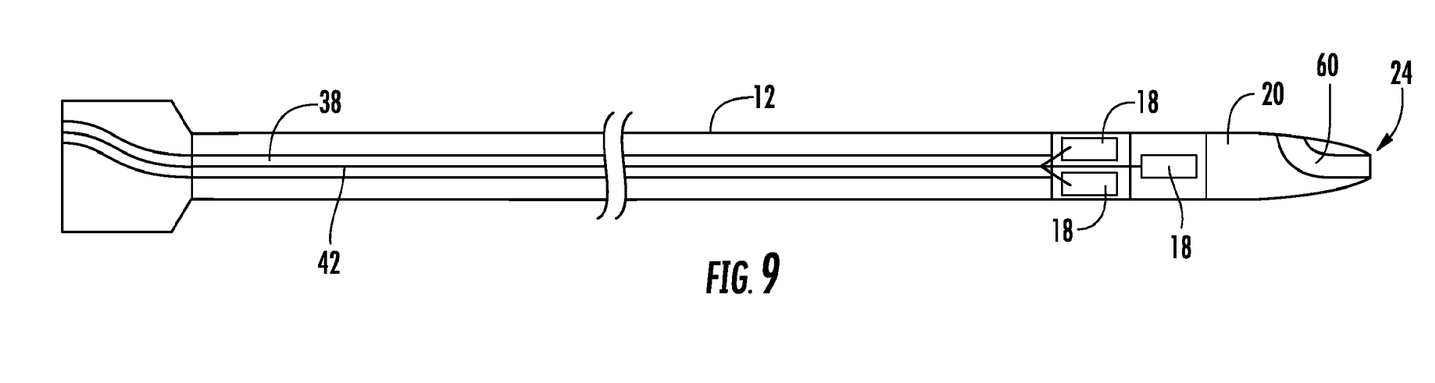
FIG. 9 is a side schematic view of a rapid exchange embodiment of the catheter of the present invention.

In an embodiment of the medical device 10 shown in FIG. 9, the medical device 10 is a rapid-exchange catheter. Accordingly, the medical device 10 further includes a guide wire exit port 60 located on or near the distal end 24 of the elongated tip 20 in order to aid in directing the medical device 10 through a vessel. Of course, the medical device 10 may be an "over-the-wire" device. In this embodiment of the medical device 10, a guidewire passes through the medical device 10 through the central lumen 38 from the proximal connector 30 to the distal end 16 of the body member 12 or distal end 24 of the elongated tip 20 if an elongated tip is used. In order for the guidewire to pass entirely through the medical device 10, the central lumen 38 must also pass through the array or arrays of transducers 18 as well as the switch 46 and elongated tip 20, if either is present.

In embodiments of the present invention involving the system 28, the system 28 may also include a patient interface module PIM 44 that facilitates communications between the medical device 10 and the remaining aspects of the system 28. In some embodiments of the system 28, the PIM 44 performs some of the functions of the computer 36 including, but not limited to, amplification, filtering, or aggregating of the data or any combination of these. Further, the PIM 44 may also supply high and low voltage AC or DC power or light to the body member 12 including for powering the transducers 18.

In use, the medical device 10 described above, is placed in a desired location, for example, by advancing the medical device 10 up the femoral artery to a desired location in the aorta. Because of the unique location of each of the transducers 18 on the outer surface 40 of the body member 12, one the medical device 10 is in a desired location, each transducer 18 is "aimed" at a different location and thus will "see" different structure (FIG. 2). With the medical device 10 in the desired location, the transducers 18 are energized so that either an ultrasonic or light wave produced by the transducers 18 leave the transducers 18 to impinge on the surrounding structure (FIG. 6). The ultrasound or light waves reflect off the surrounding structure (which could be tissue, blood or other fluid, devices, bone, etc.) at different depths and return to the transducers 18 where they are picked up by one or more transducer 18 (FIG. 6). The signal detected by each transducer 18 is sent to the computer 36 or PIM 44 to be processed.

In particular, the signal is processed to calculate the distance from each transducer to the nearest structure (e.g., the wall of the vessel in which the medical device 10 is placed). The distance is calculated using time-of-flight techniques associated with IVUS and OCT systems such as is well understood in the art.

Figure 10:
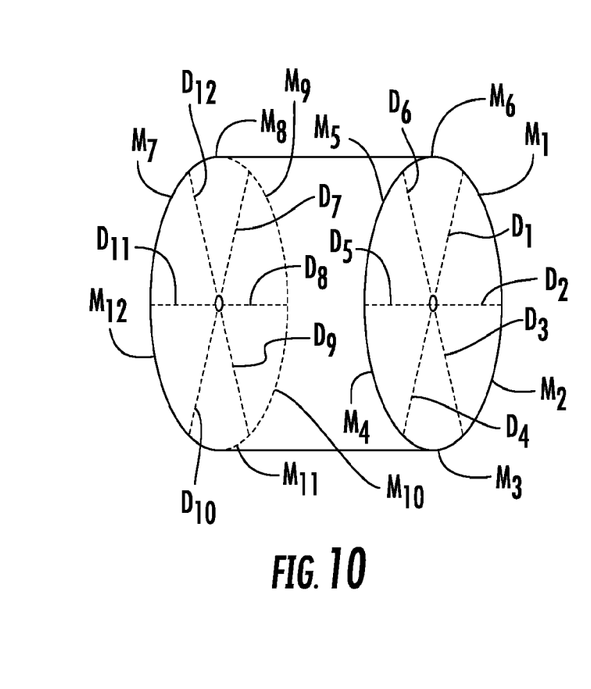
FIG. 10 is a perspective phantom view of three-dimensional map made according to the present invention.

Because each transducer 18 is uniquely aimed circumferentially around the medical device 10 (FIGS. 2 and 3A-3C), each transducer 18 will produce a signal representative of the distance from that transducer 18 to the structure nearest that transducer 18. For example as shown in FIG. 10, the medical device 10 has six transducers in each array of transducers 18. Each transducer 18 sends and receives a signal to produce respective distances $D_1$-$D_6$ in one array and distances $D_7$-$D_{12}$ in an adjacent array. When all the distances from each of the transducers 18 to their respective nearest structures are received, and because the diameter of the body member 12 where the transducers 18 are located is known, the computer 36 or PIM 44 can calculate the diameter of the cavity around the transducers 18 at any location radially from the transducers 18. This is done by taking the calculated distance from transducers 18 arranged on opposite sides of the body member 12 to their respective nearest structure (e.g., $D_1$ and $D_4$, $D_2$ and $D_5$, $D_3$ and $D_6$) and adding the diameter of the medical device 10 at the transducers 18 to determine the axial distance from one "wall" of the structure facing one transducer 18 to the "wall" of the structure facing the transducer 18 directly opposite the first transducer 18. By calculating such distances of respective pairs of transducers 18 (e.g., $D_1$ and $D_4$, $D_2$ and $D_5$, $D_3$ and $D_6$), the radial distance or diameter from one "wall" to the opposite "wall" along an axis passing through the paired transducers 18 can be determined. When several such distances are calculated and plotted radially around the medical device 10, a map of the cross-section of the structure (e.g., blood vessel, heart chamber, bladder) can be determined.

Note that this map is a two-dimensional map. But, a three-dimensional map may also be produced by the medical device 10. This may be accomplished two ways. First, in embodiments of the medical device 10 where there is more than one array of transducers (FIG. 4B), each array will produce its own two-dimensional cross-sectional map. For example, in FIG. 10 two maps are made, the first map made up of distances $D_1$-$D_6$ and connecting segments $M_1$-$M_6$ corresponding to a first array of transducers 18 and a second map made up of distances $D_7$-$D_{12}$ and connecting segments $M_7$-$M_{12}$, respectively. Because each array of transducers 18 is spaced from its neighbor array of transducers 18, the resulting two-dimensional cross-sectional maps will represent different cross-sections of the underlying structure (e.g., cross-sections separated by the spacing between each of the circumferential arrays). Combining these multiple two-dimensional maps produces a three-dimensional structure (FIG. 10).

Another way of producing a three-dimensional map is to move the medical device 10 axially forward or backwards while taking measurements. Preferably, such forward or backward axial movement is done in a controlled and measured way. By knowing the speed and direction of the pullback, the location of the respective distance measurements can be plotted to define a three-dimensional structure. For example, if a medical device 10 is in a blood vessel, for example during a veinogram, and is pulled back at a controlled rate while taking measurements of the distance from each of the transducers 18 to the wall of the blood vessel directly facing the transducer 18, a three-dimensional map of the blood vessel is produced (FIG. 11).

Figure 11:
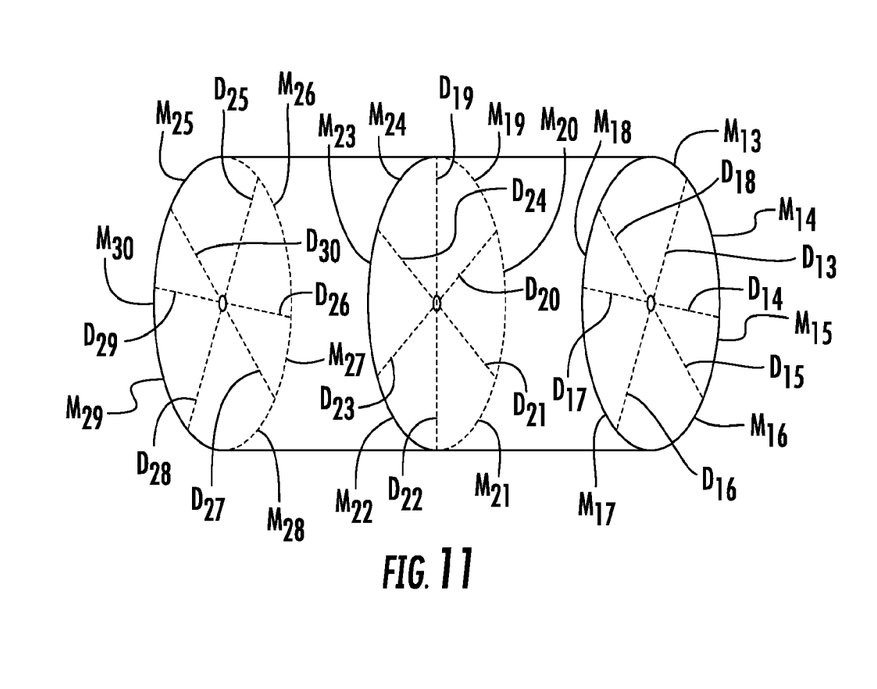
FIG. 11 is a perspective phantom view of another three-dimensional map made according to the present invention.

In the example of FIG. 11, each array of transducers 18 will produce its own two-dimensional cross-sectional map. In the example of FIG. 11 three maps are made. The first map is made up of distances $D_{13}$-$D_{18}$ and connecting segments $M_{13}$-$M_{18}$ corresponding to a first array of transducers 18. A second map is also made up of distances $D_{19}$-$D_{24}$ and connecting segments $M_{19}$-$M_{24}$, respectively. A third map is also made up of distances $D_{25}$-$D_{30}$ and connecting segments $M_{25}$-$M_{30}$, respectively. This second and/or third map can be made by either a second and/or third array of transducers 18 as described above in connection with the maps of FIG. 10 or may be made by making a first map by an array of transducers 18 and then moving that same array of transducers axially to produce the second map. In addition, a combination of both approaches to creating maps can be done so that each array of transducers 18 produces a map at a particular axial location of the medical device 10 and each array produces additional maps as the medical device 10 is being moved axially. Because each array of transducers 18 is spaced from its neighbor array of transducers 18, the resulting two-dimensional cross-sectional maps will represent different cross-sections of the underlying structure (e.g., cross-sections separated by the spacing between each of the circumferential arrays). Combining these multiple two-dimensional maps, however produced, produces a three-dimensional structure (FIG. 11).

The two or three-dimensional maps described above may be co-registered to data, figures, physiological measurements, images such as x-ray, fluoroscopy, IVUS, OCT, CT, MRI and other previous or currently acquired images or information according to known co-registration techniques.

Further, with the cross-sectional maps formed as described above, the cross-sectional area can be determined. This cross-sectional area is determined by taking the distance lines produced by the transducers 18 to calculated diameters, which distance lines are adjacent to each other circumferentially around the medical device 10, generating a line connecting the adjacent distance lines to create a two-dimensional closed substantially "pie piece" shape, calculating the area of that shape and then adding together the areas of all the shapes to get the total area of the structure around the medical device 10. Techniques for generating the lines connecting adjacent diameters to create two-dimensional closed shapes include, but are not limited to, forming straight lines, arcs of a circle, curves and splines, such as Basis splines or B-splines, and may take into consideration information from other two-dimensional cross-sectional diameters or distances from the transducers 18 to the closest tissue or structure of interest determined from other arrays of transducers 18 on the medical device 10 or from two-dimensional diameters determined from moving the medical device 10 axially as described above.

The transducers 18 of one or more arrays may be energized simultaneously so that a "snap shot" image is produced. Where the transducers 18 are energized simultaneously, the medical device 10 must be configured to be able to pass the signals produced by the various transducers 18 by receiving their respective echoes back to the computer 36 or PIM 44 to be processed. The transducers 18 of one or more arrays may also be energized in a predetermined sequence to reduce the amount of information necessary to be passed back to the computer 36 or PIM 44 at any given time. This sequential energizing of transducers 18 may be desirable when using a multiplexer switch 46 as described above.

In the embodiments of the medical device 10 that include an angioplasty balloon 48, the medical device 10 is located in a vessel such as a coronary artery so that the angioplasty balloon 48 is at a desired location. Fluid is passed into the inflation port 58 where it travels through the duct 56 to inflate the angioplasty balloon 48 as is well understood in the art. The transducers 18 may be fired before, during and after activation of the angioplasty balloon 48 to assist in correctly locating the angioplasty balloon 48, ensuring that the angioplasty balloon is inflating correctly and is applying the desired therapy (e.g., the vessel diameter is increasing) and confirming that the angioplasty procedure was successful after the angioplasty balloon 48 is deflated but before the medical device 10 is removed. The transducers 18 are operated and the diameter of the vessel determined as described above.

Figure 8:
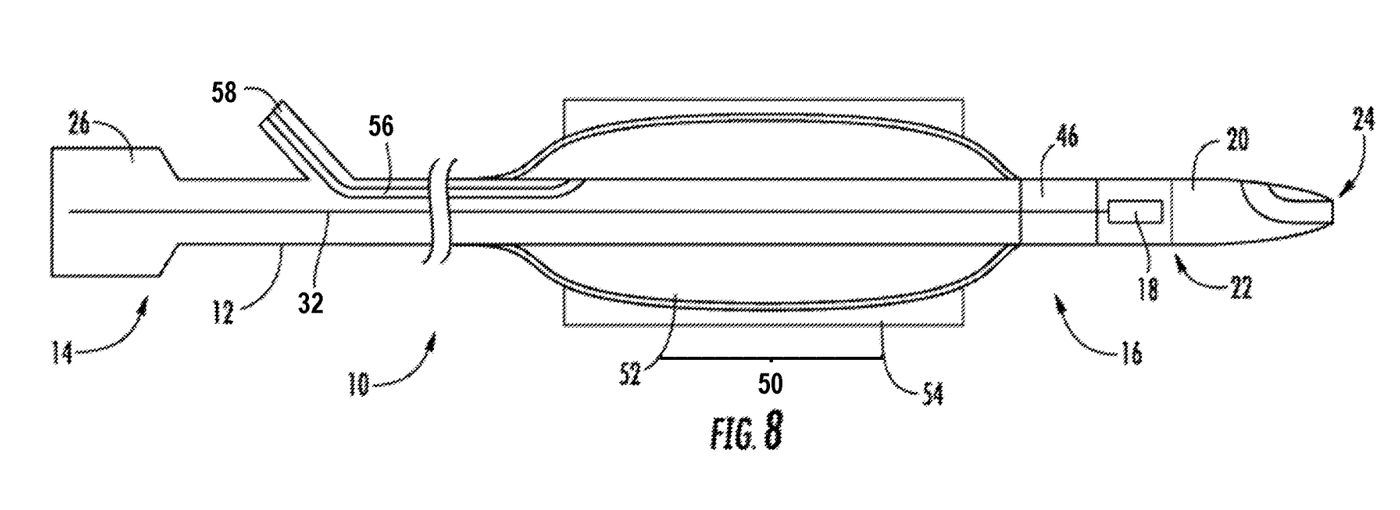
FIG. 8 is a side schematic view of an embodiment of the catheter of the present invention having a stent deployment balloon and a stent.

In embodiments of the medical device 10 that include a stent delivery balloon and stent assembly 50, again the medical device 10 is located in a vessel such as a coronary artery so that the stent deployment balloon 52 of the stent delivery balloon and stent assembly 50 is at a desired location. Fluid is passed into the inflation port 58 where it travels through the duct 56 to inflate the stent deployment balloon 52 as is well understood in the art. Again, the transducers 18 are fired, as described above, before, during and after activation of the stent deployment balloon 52 to assist in correctly locating the stent 54, ensuring that the stent deployment balloon 52 is inflating correctly and is applying the desired therapy (e.g., the vessel diameter is increasing and the stent 54 is deploying) and confirming that the stent 54 was successfully and fully deployed after the stent deployment balloon 52 is deflated but before the medical device 10 is removed. The transducers 18 are operated and the diameter of the vessel determined as described above. This embodiment of the medical device 10 confirms that the stent 54 is fully deployed and that the correct stent 54 is used. In the embodiments using either an angioplasty balloon 48 or a stent delivery balloon and stent assembly 50, the preferred number of transducers 18 placed circumferentially around the body member 12 is from six to eight although fewer or more transducers 18 may be used depending on where the medical device 10 is used, the frequency of the emitted ultrasound or light signals, among the possible considerations.

The present invention has applicability wherever it is desirable to know the cross-sectional dimensions the space surrounding the device. Illustrative examples of these applications include, but are not limited to, diagnosing or treating non-thrombotic venous disease, coronary stable angina, placing or retrieving inferior vena cava (IVC) filters, replacing or repairing heart valves, placing peripheral drug eluting balloons (DEB), Throughout this description, mention has been made of placing the medical device 10 in vessels. Vessel, as used herein, means any fluid filled structure or structure surround by fluid within a living body or, where ultrasound is not use, any structure that may be imaged and includes both natural and man-made structures. Examples of such vessels include, but are not limited to, organs including the heart, arteries, veins, liver, kidneys, gall bladder, pancreas, lungs, breasts; ducts; intestines; nervous system structures including the brain, dural sac, spinal cord and peripheral nerves; the urinary tract; rectum; vagina; as well as valves within the blood or other systems of the body. In addition to the previously listed natural structures, the medical device 10 may be used as described herein to calculate dimensions, image or otherwise take data on such man-made structures as, without limitation, heart valves, stents, shunts, filters and other devices positioned within the body, for example, a guide wire or guide catheter.

While the above description contains many specifics, these should not be construed as limitations on the scope of the invention, but rather as examples of preferred embodiments thereof. As a result, the description contained herein is intended to be illustrative and not exhaustive. Many variations and alternatives of the described technique and method will occur to one of ordinary skill in this art. Further, the medical device 10 has been described in connection with producing maps of the distance from the transducers 18 to the tissue of structure opposite the transducers 18 or the area around the transducers 18. But, the medical device 10 may also be used to produce images such as intravascular ultrasound (IVUS) or OCT images as is well understood in the art.

Variations in form of the component pieces described and shown in the drawings may be made as will occur to those skilled in the art. Further, although certain embodiments of a medical device 10 have been described, it is also within the scope of the invention to add other additional components or to remove certain components such as the elongated tip 20, multiple arrays of transducers 18, switches 46 or proximal connectors 26. Also, variations in the shape or relative dimensions of all of the various components of the medical device 10 or system 28 will occur to those skilled in the art and still be within the scope of the invention.

All these alternatives and variation are intended to be included within the scope of the attached claims. Those familiar with the art may recognize other equivalents to the specific embodiments described herein which equivalents are also intended to be encompasses by the claims attached hereto. As a result, while the above description contains many specifics, these should not be construed as limitations on the scope of the invention but rather as examples of different embodiment thereof.

What is claimed is:

1. A method for generating a cross-sectional computed map of a vascular fluid filled structure, comprising:
   inserting a catheter into a vascular fluid filled structure, the catheter having an elongated flexible body member with a plurality of transducers circumferentially separated and distributed about an outer surface of a distal end of the body member, the plurality of transducers being fixed relative to the body member so as to not rotationally vibrate relative to the body member;
   activating each transducer of the plurality of separated ultrasound transducers and transmitting a signal from each transducer toward a portion of the structure perpendicular to the transducer;
   receiving at each separated transducer a reflected ultrasound signal from a respective circumferentially separated section of the structure;
   in response to receiving the reflected ultrasound signal at each separated transducer, generating from each transducer an electrical signal representative of the reflected ultrasound signal from each circumferentially separated section of the structure;
   plotting circumferentially separated coordinate points of the structure by calculating radial distances to the circumferentially separated section of the structure based on the respective reflected ultrasound electrical signals; and generating a computed map image in a computer display that comprises calculating and plotting a cross-sectional map of the structure by interpolating between the circumferentially separated coordinate points of the structure.

2. The method of claim 1, further comprising co-registering the computed map image with at least one of other measurement data, figures, physiological measurements, x-ray, fluoroscopy, intravascular ultrasound (IVUS), optical coherence tomography (OCT), computed tomography (CT), or magnetic resonance imaging (MRI).

3. The method of claim 1, wherein the plurality of transducers includes a first and a second array of transducers, where the second array of transducers is longitudinally spaced apart along the elongated flexible body by a predefined distance from the first array of transducers.

4. The method of claim 3, wherein generating the computed map image comprises plotting a first cross-sectional map respective to the calculated radial distances for the first array of transducers and plotting a second cross-sectional map respective to the calculated radial distances for the second array of transducers, wherein the plotting of the of first cross-sectional map is offset from the second cross-sectional map based on the predefined distance.

5. The method of claim 4, wherein generating the computed map image comprises plotting lines connecting portions of the first cross-sectional map with corresponding portions of the second cross-sectional map.

6. The method of claim 1, wherein the plotted lines are based on one or more of calculating straight lines, arcs of a circle, curves, splines, Basis splines, and B-splines.

7. The method of claim 1, further comprising:
after activating each transducer and receiving a reflected signal at each respective transducer, axially repositioning the catheter by a determined longitudinal distance from its position at which the transducers were activated; and
respective to the position at which the catheter has been repositioned, repeating the steps of activating each of the transducers, receiving a reflected signal at each of the respective transducers, calculating a radial distance between each transducer and the respective section of the structure, and plotting circumferentially separated coordinate points of the structure based on the respective calculated distance;
wherein generating the computed map image comprises calculating and plotting first and second cross-sectional maps respective to the positions of the catheter before and after axially repositioning the catheter, the first and second cross-sectional maps offset from each other based on the determined longitudinal distance.

8. The method of claim 7, wherein the computed map image represents a longitudinal extent of the structure.

9. The method of claim 7, further comprising generating a three-dimensional representation of the lumen based on said first and second cross-sectional maps.

10. The method of claim 1, wherein a plurality of the ultrasound transducers are energized substantially simultaneously.

11. The method of claim 1, wherein a plurality of the ultrasound transducers are energized in a predetermined sequence to reduce the amount of information simultaneously passed to a processor receiving the electrical signals generated from each transducer.

12. The method of claim 11, wherein the electrical signals generated from the plurality of transducers are distributed through a switch that is selectively actuated based on a selected transducer.

13. The method of claim 12, wherein the switch comprises a multiplexor.

14. The method of claim 1, further comprising calculating a diameter of the fluid-filled structure based on the cross-sectional map of the structure.

15. The method of claim 1, further comprising calculating a cross-sectional area of the fluid-filled structure by calculating an area of a closed shape based on the cross-sectional map of the structure.

16. The method of claim 1, wherein the interpolating comprises calculating splines based on the separated coordinate points of the structure.

17. The method of claim 1, wherein the catheter comprises an angioplasty balloon and wherein the method further comprises using the cross-sectional map to at least one of position or control the expansion of the angioplasty balloon for performing an angioplasty procedure.

18. The method of claim 1, further comprising:
performing an angioplasty procedure using the catheter; and
after deflating an angioplasty balloon used during the angioplasty procedure, calculating a level of expansion of at least one of the lumen or a stent expanded during the angioplasty procedure, the calculated expansion based on the cross-sectional map.

19. The method of claim 1, wherein each of the plurality of transducers is not directly adjacent to any other transducer.

20. The method of claim 19, wherein the plurality of transducers comprises 4 or 8 transducers.

* * * * *

UNITED STATES PATENT AND TRADEMARK OFFICE
CERTIFICATE OF CORRECTION

| | |
|---|---|
| PATENT NO. | : 12,064,288 B2 |
| APPLICATION NO. | : 16/264449 |
| DATED | : August 20, 2024 |
| INVENTOR(S) | : Stephen Eric Ryan |

It is certified that error appears in the above-identified patent and that said Letters Patent is hereby corrected as shown below:

In the Specification

Column 1, Line 11, delete "reference" and insert -- reference. --.

Column 10, Line 1, delete "veinogram," and insert -- venogram, --.

Column 11, Line 54, delete "(DEB)," and insert -- (DEB). --.

In the Claims

Column 13, Line 23, Claim 4, delete "the of" and insert -- the --.

Signed and Sealed this
Twenty-second Day of October, 2024

Katherine Kelly Vidal
*Director of the United States Patent and Trademark Office*